US010973800B2

(12) United States Patent
Liu

(10) Patent No.: US 10,973,800 B2
(45) Date of Patent: Apr. 13, 2021

(54) SALVINORIN COMPOSITIONS AND USES THEREOF

(75) Inventor: Renyu Liu, Media, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 753 days.

(21) Appl. No.: 13/806,068

(22) PCT Filed: Jun. 29, 2011

(86) PCT No.: PCT/US2011/042427
§ 371 (c)(1),
(2), (4) Date: Dec. 20, 2012

(87) PCT Pub. No.: WO2012/006178
PCT Pub. Date: Jan. 12, 2012

(65) Prior Publication Data
US 2013/0102659 A1 Apr. 25, 2013

Related U.S. Application Data

(60) Provisional application No. 61/359,611, filed on Jun. 29, 2010.

(51) Int. Cl.
*A61K 31/366* (2006.01)
*A61K 36/537* (2006.01)

(52) U.S. Cl.
CPC .......... *A61K 31/366* (2013.01); *A61K 36/537* (2013.01)

(58) Field of Classification Search
CPC .................................................. A61K 31/366
USPC ................................................ 514/244, 455
See application file for complete search history.

(56) References Cited

U.S. PATENT DOCUMENTS

| 2006/0052439 | A1 | 3/2006 | Beguin |
| 2007/0213394 | A1 | 9/2007 | Beguin |
| 2009/0203761 | A1 | 8/2009 | Schubert et al. |
| 2010/0093872 | A1 | 4/2010 | Loduca Blomberg et al. |
| 2012/0149564 | A1 | 6/2012 | Tam et al. |
| 2013/0102659 | A1 | 4/2013 | Liu et al. |

FOREIGN PATENT DOCUMENTS

| WO | WO 2005/089745 | 9/2005 |
| WO | WO2007100775 A2 * | 9/2007 |
| WO | WO2008/119097 | 10/2008 |

OTHER PUBLICATIONS

Wang et al., Effect of salvia miltiorrhiza and cerebral vascular spasm induced by experimental SAH in rabbits, Henan Journal of Practical Neurons Diseases, Apr. 2003, p. 1, abstract.*
Koudstaal et al. Headache in Transient or Permanent Cerebral IschemiaStroke (1991) vol. 22, pp. 754-759.*
Mayfield Brain & Spine (2009) pp. 1-3 Retrieved on Sep. 20, 2016, Retrieved from the internet:<url:http://www.mayfieldclinic.com/PESAH.HTM>.*
Hooker et al. NeuroImage (2008), vol. 41, pp. 1044-1050.*
Hijdra et al. Stroke (1988) vol. 19, pp. 1250-1256.*
Zeynalov et al. Journal of Cerebral Blood Flow & Metabolism (2006), vol. 26, pp. 414-420.*
Kasumoto et al. Recent Advance in Neurotraumology (1993), vol. pp. 240-243.*
Pluta et al. Neurol Res. (2009), vol. 31, pp. 151-158.*
Birch et al. (Br. J. Pharmacol . . . (1991), vol. 103, p. 1819-1823) (Year: 1991).*
Roth et al. PNAS (2002) vol. 99, p. 11934-11939 (Year: 2002).*
Roth et al., "Salvinorin A: a potent naturally occurring nonnitrogenous kappa opioid selective agonist" Proc. Natl. Acad. Sci. USA 99:11934 (2002).
Butelman et al., Psychopharmacology 172:220 (2004).
Sefton, "Implantable pumps", CRC Crit. Ref. Biomed. Eng. 14:201 (1987).
Buchwald et al. "Long-term, continuous intravenous heparin administration by an implantable infusion pump in ambulatory patients with recurrent venous thrombosis." Surgery 88:507 (1980).
Saudek et al."A preliminary trial of the programmable implantable medication system for insulin delivery." N. Engl. J. Med. 321:574 (1989).
Goodson, in Medical Applications of Controlled Release, supra, vol. 2, pp. 115-138 (1984).
Langer, "New methods of drug delivery", Science 249:1527-1533 (1990).
Abuchowski et al. "Immunosuppressive properties and circulating life of Achromobacter glutaminase-asparaginase covalently attached to polyethylene glycol in man" Cancer Treat Rep. 65(11-12):1077-81 1981.
Katre et al. "Chemical modification of recombinant interleukin 2 by polyethylene glycol increases its potency in the murine Meth A sarcoma model" Proc Natl Acad Sci U S A. 84(6):1487-91. Mar. 1987.
Xu et al., Recent advance on research and application of salvia militiorrhiza, Asian Journal of Pharmacodynamics and Pharmacokinetecs, 2007, vol. 7(2), pp. 99-130.
Wang et al., "Effect of Salvia militiorrhiza and cerebral vascular spasm induced by experimental SAH in rabbits", Henan Journal of Practical Neurons Diseases, 2003-2004, abstract only.
Endoh et al., "The influence of nicardipine-, nitroglycerin-, and prostaglandin E1—induced hypotension on cerebral pressure autoregulation in adult patients during propofol-fentanyl anesthesia", Anesth. Analg. 2002, vol. 94, pp. 169-173.
Bleske et al. "Comparison of intravenous and intranasal administration of epinephrine during CPR in a canine model. Annals of emergency medicine" Sep. 1, 1992;21(9):1125-30, Abstract.
EMCDA salvia divinorurn drug profile. [oonline] retrieved on Jul. 13, 2016: url:http://wwwemcdda.europa.eu/publications/drug-profiles/salvia.

(Continued)

*Primary Examiner* — Taina D Matos Negron
(74) *Attorney, Agent, or Firm* — Mark S. Cohen; Pearl Cohen Zedek Latzer Baratz LLP

(57) ABSTRACT

The invention relates to salvinorin compositions and uses thereof. Specifically, the invention relates to administering a salvinorin compound to produce vasodilatory effect and organ protective effect from hypoxia/ischemia and reperfusion. The invention further relates to treating various diseases or disorders.

12 Claims, 17 Drawing Sheets

(56) References Cited

OTHER PUBLICATIONS

Figure 1:
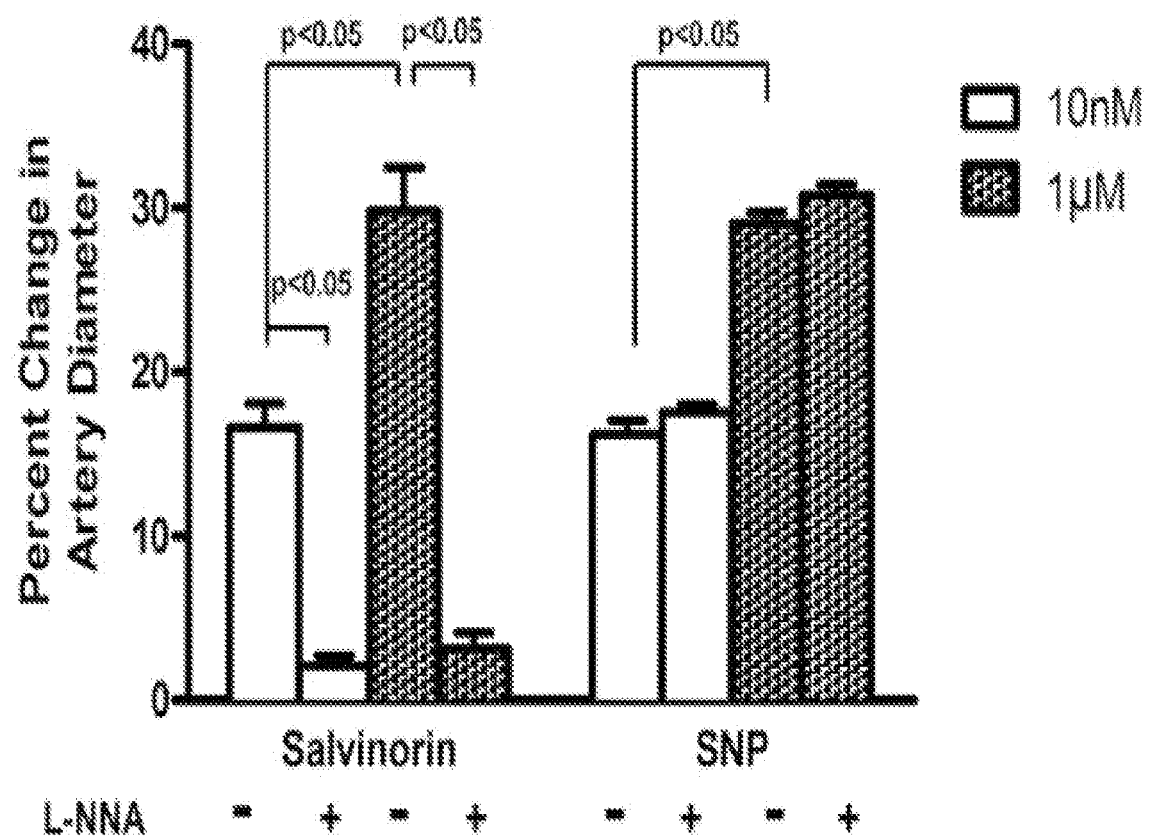

Filion et al. "Perioperative use of cardiac medical therapy among patients undergoing coronary artery bypass graft surgery: a systematic review" American heart journal, Sep. 30, 2007;154(3):407-14.
Gallimore, D. "Understanding the drugs used during cardiac arrest response" Nurs Times. Jun. 6, 2006;102(23):24-6.
Inamasu et al. "Subarachnoid haemorrhage as a cause of out-of-hospital cardiac arrest: a prospective computed tomography study", Resuscitation. Sep. 30, 2009;80(9):977-80.
Ji et al., "Herkinorin dilates cerebral vessels via kappa opioid receptor and cyclic adenosine monophosphate (cAMP) in a piglet model", Brain Res. 2013, 1490: 95-100.
Manole et al. "Post-cardiac arrest syndrome: Focus on the brain" Current opinion in pediatrics. Dec. 2009;21(6):745.
Nelson KB "Perinatal ischemic stroke" Stroke. Feb. 1, 2007;38(2):742-5.
Newmark et al., "Tuberous Sclerosis evaluated by Computerized Tomography", Computerized Radiol. 1982, vol. 6, pp. 287-293.
Palmer et al. "Symptomatic subarachnoid hemorrhage in the term newborn" Journal of perinatology: official journal of the California Perinatal Association. Jun. 1991;11(2):112-6.
Pluta et al. "Early blood-brain barrier changes in the rat following transient complete cerebral ischemia induced by cardiac arrest" Brain research. Jun. 7, 1994;633(1-2):41-52.
Roquette [Online] Hydroxypropyl Betacyclodextrin an Enabling Technology for Challenging Pharmaceutical Formulation, 4 pages.
Su et al., "Salvinorin A pretreatment preserves cerebrovascular autoregulation after brain hypoxic/ischemic injury via extracellular signal-regulated kinase/mitogen-activated protein kinase in piglets", Anesth. Analg. 2012, 114: 200-204.
Su et al., "Salvinorin A produces cerebrovasodilation through activation of nitric oxide synthase, κ receptor, and adenosine triphosphate-sensitive potassium channel", Anesthesiology 2011, 114: 374-379.
Wang et al., "Salvinorin A administration after global cerebral hypoxia/ischemia preserves cerebrovascular autoregulation via kappa opioid receptor in piglets", PloS One, 2012, 7: e41724.
Zhang e al. "Kappa-opioid receptor selectivity for ischemic neuroprotection with BRL 52537 in rats" Anesthesia & Analgesia. Dec. 1, 2003;97(6):1776-83.

\* cited by examiner

Before salvinorin  After Salvinorin

Image of Salvinorin A

FIGURE 8

Image of Cucurbit[7]uril

Salvinorin Cucurbituril7 complex

SALVINORIN COMPOSITIONS AND USES THEREOF

CROSS-REFERENCE TO RELATED APPLICATIONS

This application is a National Phase Application of PCT International Application No. PCT/US11/42427, International Filing Date Jun. 29, 2011, claiming priority to United States Provisional Patent Application 61/359,611, filed Jun. 29, 2010, all of which are incorporated by reference herein in their entirety.

FIELD OF THE INVENTION

The invention relates to salvinorin compositions and uses thereof. Specifically, the invention relates to administering a salvinorin compound to produce vasodilatory, organ protective effect from hypoxia/ischemia and reperfusion. The invention further relates to treating various diseases or disorders.

BACKGROUND OF THE INVENTION

Salvinorin A is an active component of *Salvia Divinorum,* a perennial herb of the Lamiaceae (mint) family, indigenous to Mexico. *Salvia divinorum* has long been traditionally used to produce hallucinogenic experiences essential for spiritual divination. It has been shown that salvinorin A is the most highly efficacious, naturally-occurring, nonpeptide, and the only non-nitrogenous kappa opioid receptor (KOR) agonist.

Similar to the history of opium, *Salvia Divinorum* as a natural abundant plant has been used by human being for recreational purposes for several centuries, and it has been proposed that salvinorin A could be a potential new opioid receptor agonist to be used in clinical practice, i.e. to treat depression or addiction etc. However, no convincing data obtained for these applications yet. None of KOR agonist has been used clinically so far because of their side effects. Salvinorin A doesn't belong to opioids despite it is a KOR agonist and is banned in many counties and many states in the United States. Unlike other KOR agonists, salvinorin A doesn't produce frank hallucinatory effects, and has no dysphoria actions. Many intrinsic characters of the compound, i.e. quick onset, short acting, and no reported respiratory depression, etc., made it an attractive possible medication used for patients in perioperative period and in critically illed conditions in well-controlled settings.

Accordingly, there exists a need for exploring new uses of salvinorin as a clinical medication to treat various diseases and disorders.

SUMMARY OF THE INVENTION

In one embodiment, the invention provides a method for treating a disease associated with a cerebrovasospasm, in a subject, the method comprising: administering to said subject a therapeutically effective amount of a salvinorin or a pharmaceutical composition thereof, thereby treating said disease.

In another embodiment, the invention provides a method for producing a cerebrovasodilation, in a subject, the method comprising: administering to said subject a therapeutically effective amount of a salvinorin or a pharmaceutical composition thereof, thereby producing said cerebrovasodilation.

In another embodiment, the invention provides a method for treating a disease associated with a neuronal hypoxia and/or ischemia in a subject, the method comprising: administering to said subject a therapeutically effective amount of a salvinorin or a pharmaceutical composition thereof, thereby treating said disease.

In another embodiment, the invention provides a method for producing a sedative or anesthetic effect in a subject, the method comprising: administering to said subject a therapeutically effective amount of a salvinorin or a pharmaceutical composition thereof, thereby producing said sedative or anti-nociceptive effect.

In another embodiment, the invention provides a pharmaceutical composition comprising: a therapeutically effective amount of a salvinorin, wherein said salvinorin is present in an amount effective to produce a cerebrovasodilation, organ protective effect from hypoxia and ischemia/reperfusion injury, and a sedative effect or an anti-nociceptive effect in a subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 1. Salvinorin A dose-dependently dilated brain pial artery of piglet. L-NNA, a Nitric Oxide Synthase Inhibitor, blocks the dilation effects of salvinorin but not SNP. L-NNA: N(G)-nitro-L-arginine; SNP: sodium nitroprusside.

FIG. 2. Salvinorin A increases cGMP in the CSF, and L-NNA blocked salvinorin induced cGMP elevation and vascular dilation. cGMP: cyclic guanosine monophosphate; CSF: cerebrospinal fluid; L-NNA; N(G)-nitro-L-arginine.

FIG. 3. Glibenclamide, but not Iberiotoxin, blocked the dilation effects of salvinorin A. Glibenclamide given with Iberiotoxin in any sequences blocked the dilation effects of salvinorin. S: salvinorin A; Glib: glibenclamide; Iberi: Iberiotoxin; *: the agent administered first.

FIG. 4. Glibenclamide, but not iberiotoxin, blocks the dilation effects of cromakalim and CGRP. Iberiotoxin but not glibenclamide block the dilation effects of NS1619. Panel A demonstrates the effects of 10 nM of cromakalim, CGRP and NS1619, in the presence or absence of the pretreatment agents. Panel B demonstrates the effects of 1 μM of cromakalim, CGRP and NS1619. Glib: glibenclamide; Iberi: Iberiotoxin; *: the agent administered first.

FIG. 5. Naloxone blocks the dilation effects of salvinorin and Met-enkaphlin but not isoprotenol.

FIG. 6. Salvinorin A dilated the constricted pial artery induced by hypocapnia in a dose-dependent manner.

FIG. 7. Adding 1 μM of salvinorin A over the pial artery dilated the vessel immediately within seconds. It dilated the artery ~40% and the vessel diameter returned to baseline within 5 minutes.

Figure 8:
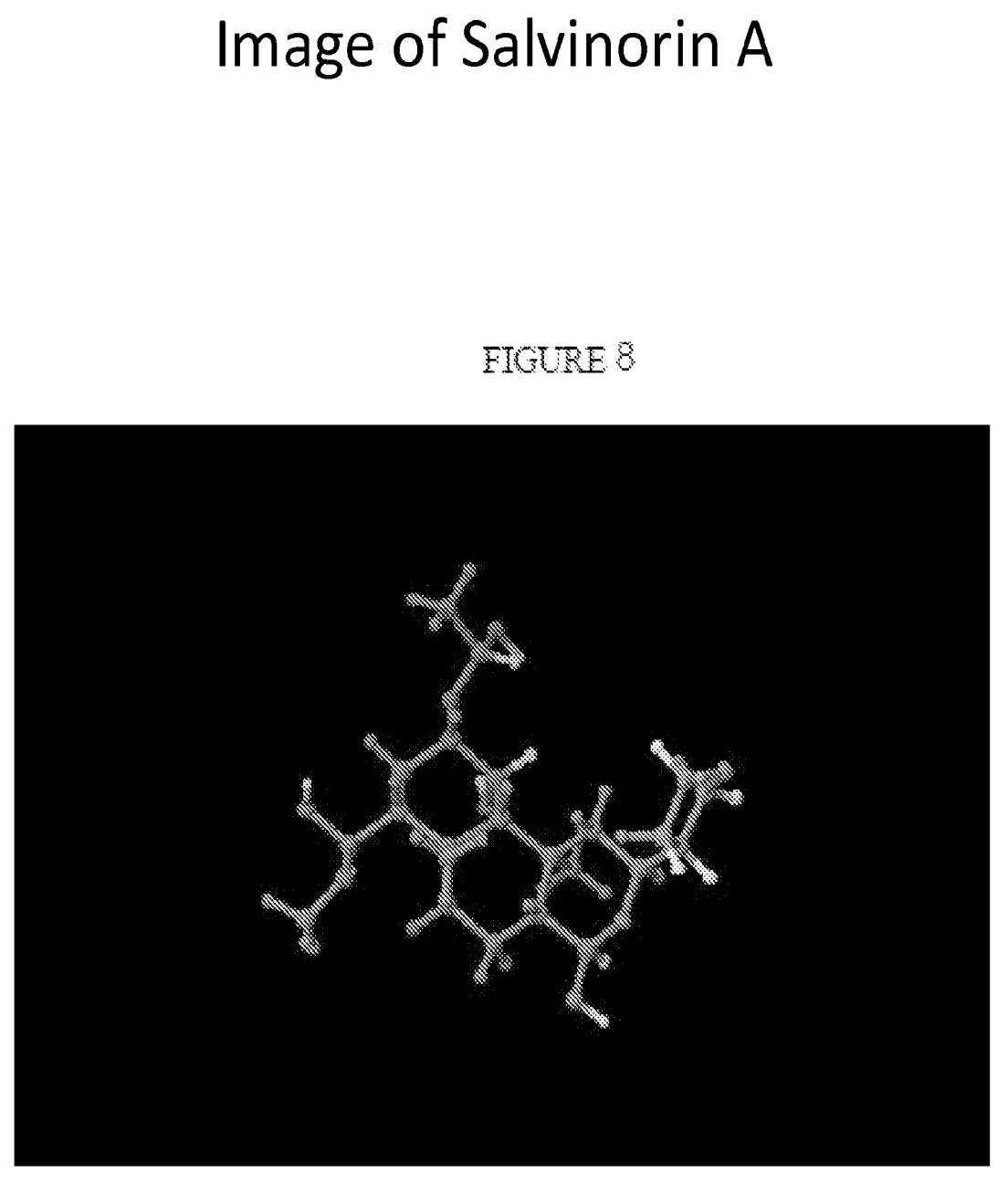

FIG. 8 illustrates an image of salvinorin A, according to one embodiment of the invention.

FIG. 9 illustrates an image of cucurbituril, according to one embodiment of the invention.

Figure 10:
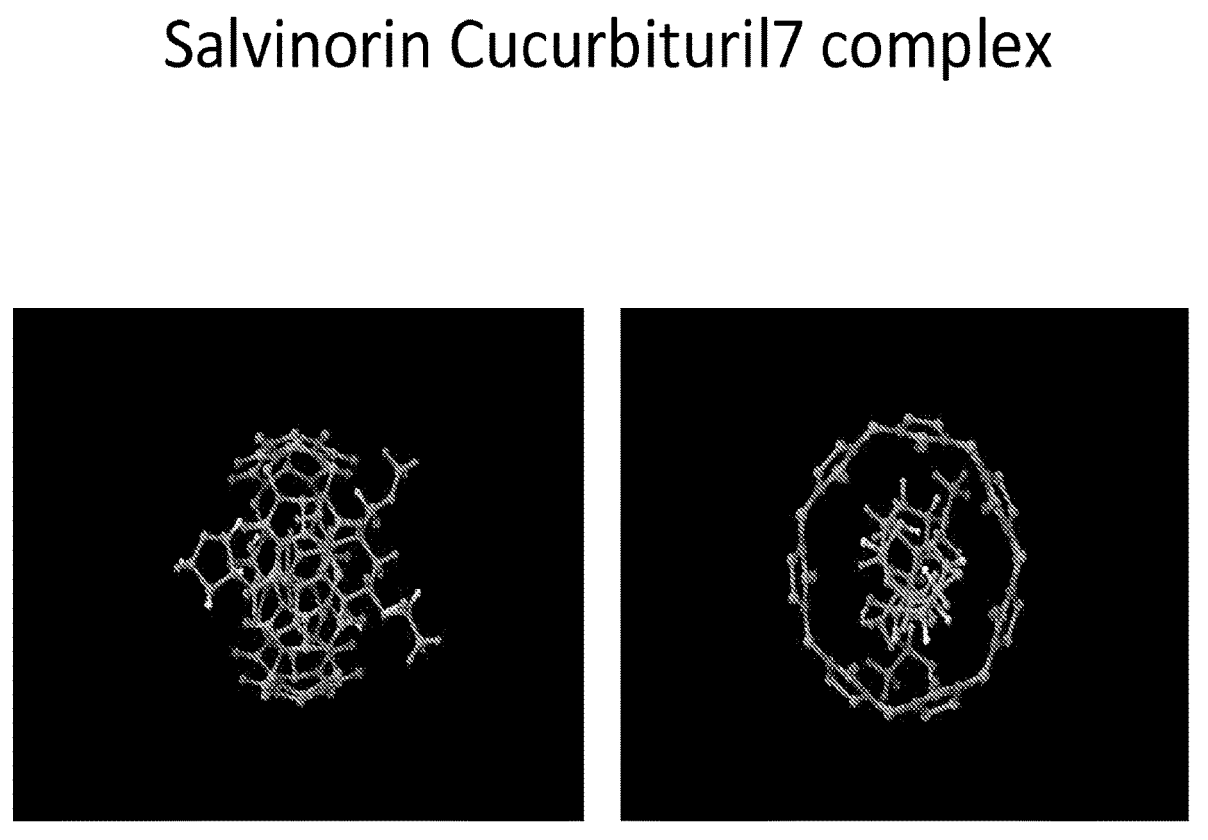

FIG. 10 illustrates an image of salvinorin-cucurbituril complex, according to one embodiment of the invention.

Figure 11:
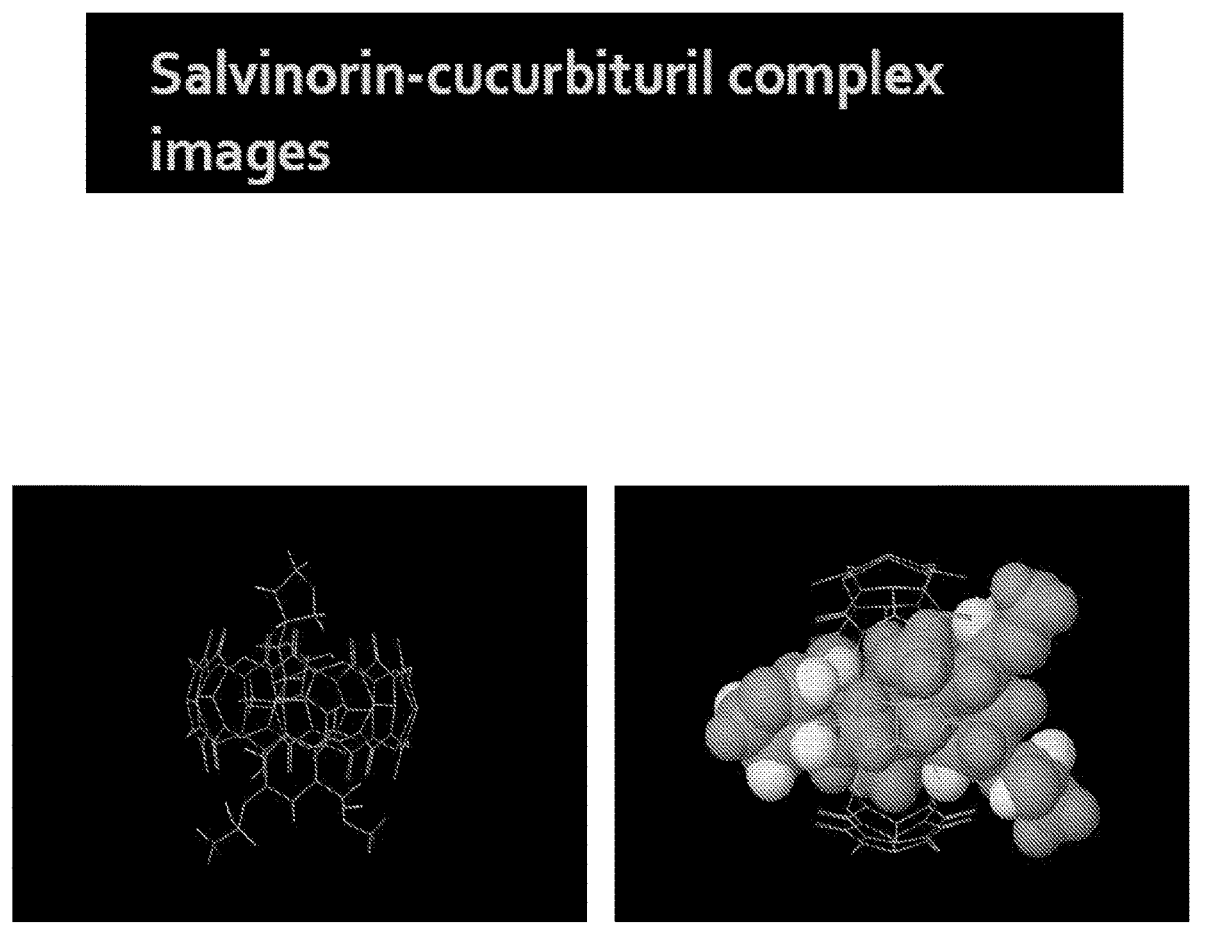

FIG. 11 illustrates an image of salvinorin-cucurbituril complex, according to one embodiment of the invention.

Figure 12:
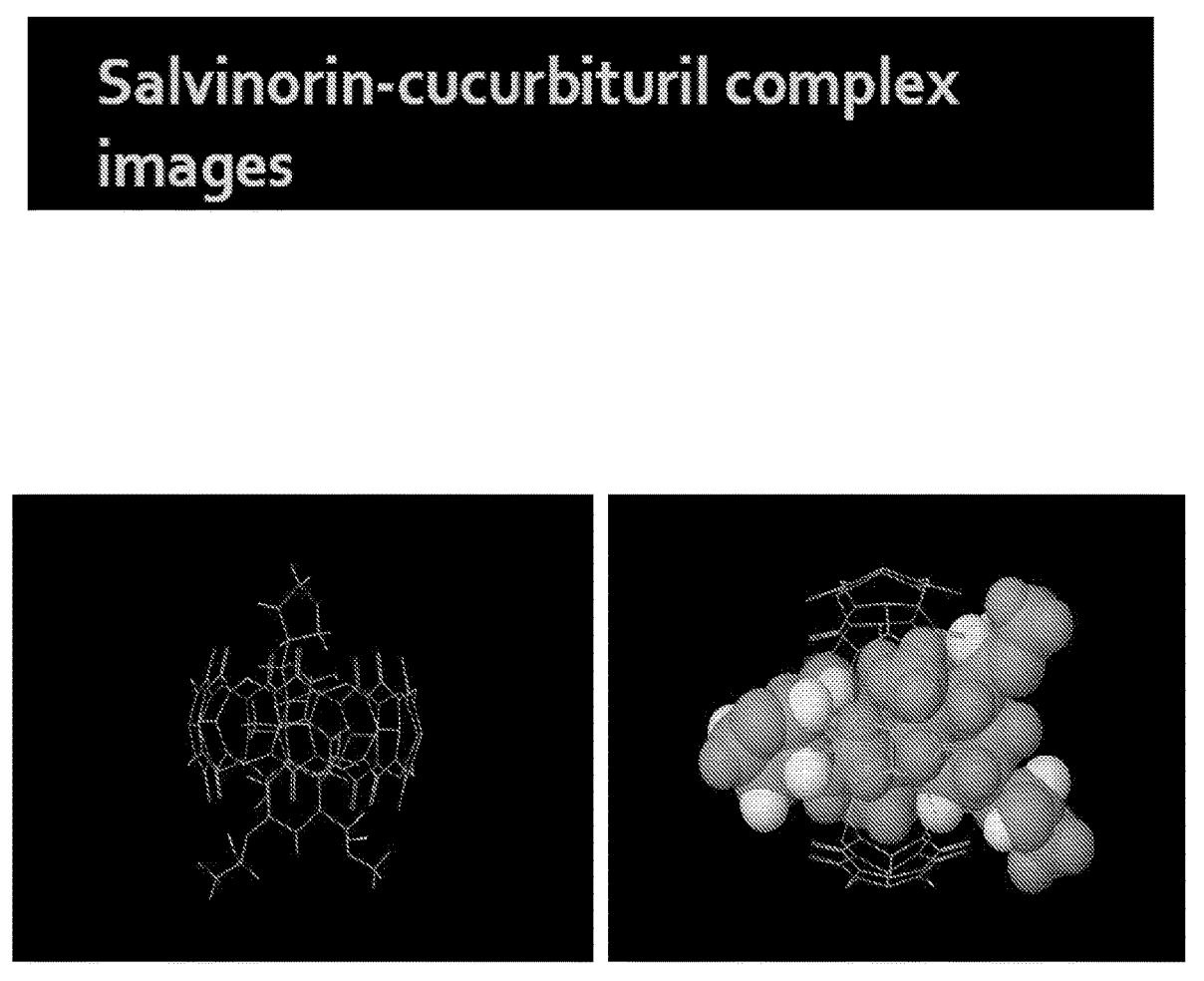

FIG. 12 illustrates an image of salvinorin-cucurbituril complex, according to one embodiment of the invention.

Figure 13:
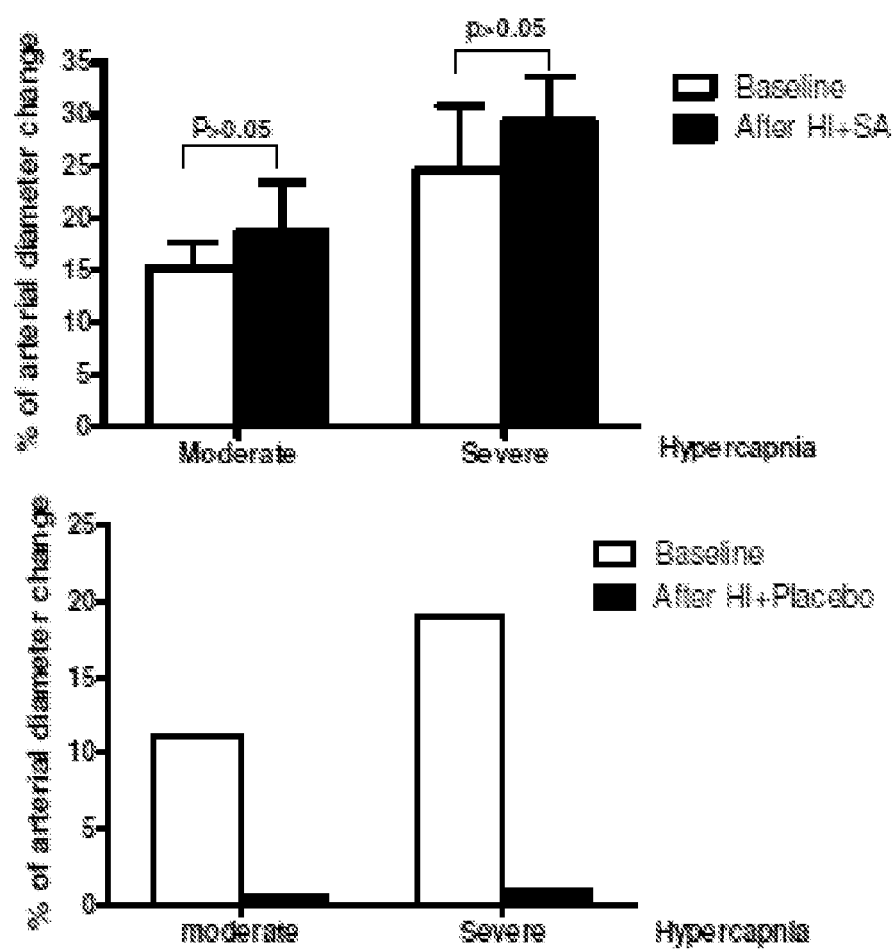

FIG. 13 shows Salvinorin A preserves brain autoregulation from hypoxia/ischemia administered immediate after hypoxia/ischemia. Upper panel shows that cerebral vascular autoregulation to hypercarbia preserved well with salvinorin administration immediately after global brain hypoxia and ischemia (n=3). Lower panel shows that cerebral vascular autoregulation is disrupted after hypoxia/ischemia (HI). Moderate and severe hypercarbia: $PaCO_2$=50 mmHg and 70 mmHg respectively. HI denotes hypoxia/ischemia and SA denotes salvinorin.

Figure 14:
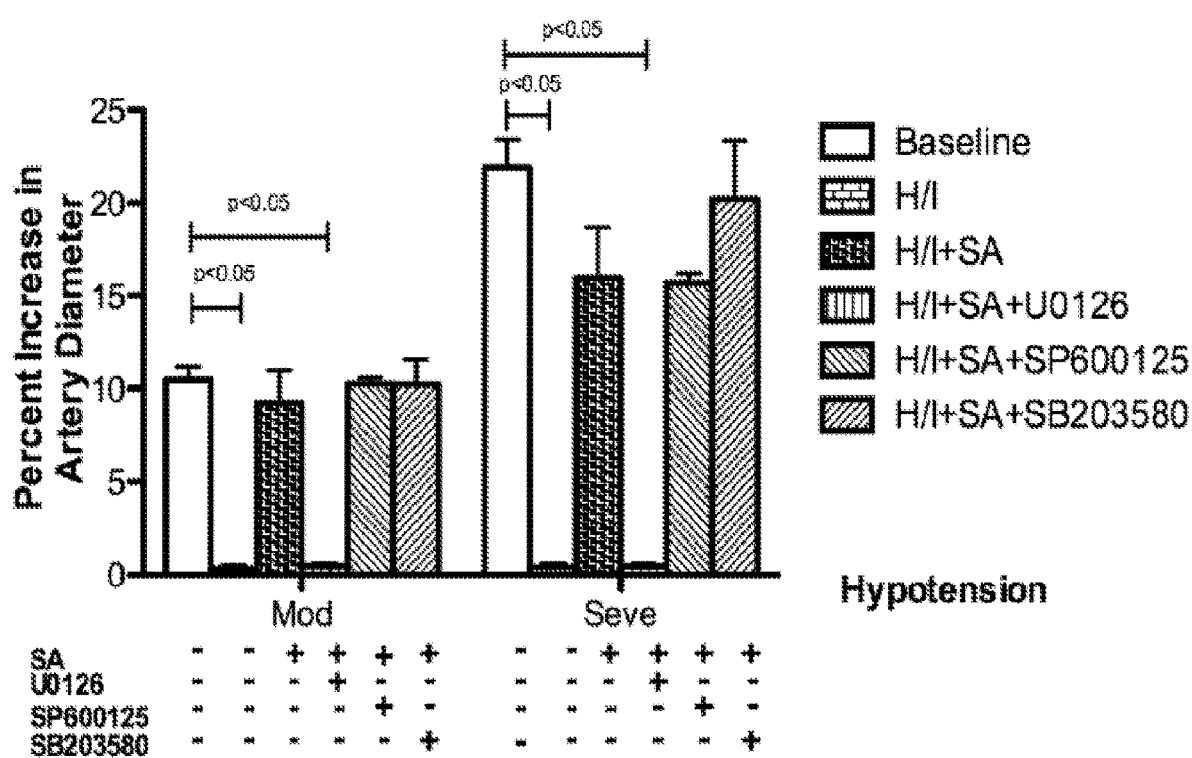

FIG. 14 shows effects of hypotension on pial artery diameter before (baseline), after hypoxia/ischemia (H/I; $PO_2$ of 35 mm Hg for 10 minutes followed by global cerebral ischemia for 20 minutes), after H/I pretreated with salvinorin A (10 μg/kg i.v.; H/I+SA) 30 minutes before H/I, and after H/I pretreated with U0126 (1 mg/kg, i.v.; H/I+SA+U0126), the antagonist of ERK, 30 minutes before salvinorin A, SP600125 (1 μM, administrated topically; H/I+SA+SP600125), the antagonist of JNK, 30 minutes before salvinorin A, SB203580 (10 μM, administrated topically; H/I+SA+SB203580), the antagonist of P38, 30 minutes before salvinorin A. Pretreatment with salvinorin A preserved the dilation response of pial artery to hypotension, which is abolished by U0126. SA: Salvinorin A; H/I: Hypoxia/ischemia; Moderate: moderate hypotension (25% decrease of mean artery pressure); Severe: severe hypotension (45% decrease of mean artery pressure).

Figure 15:
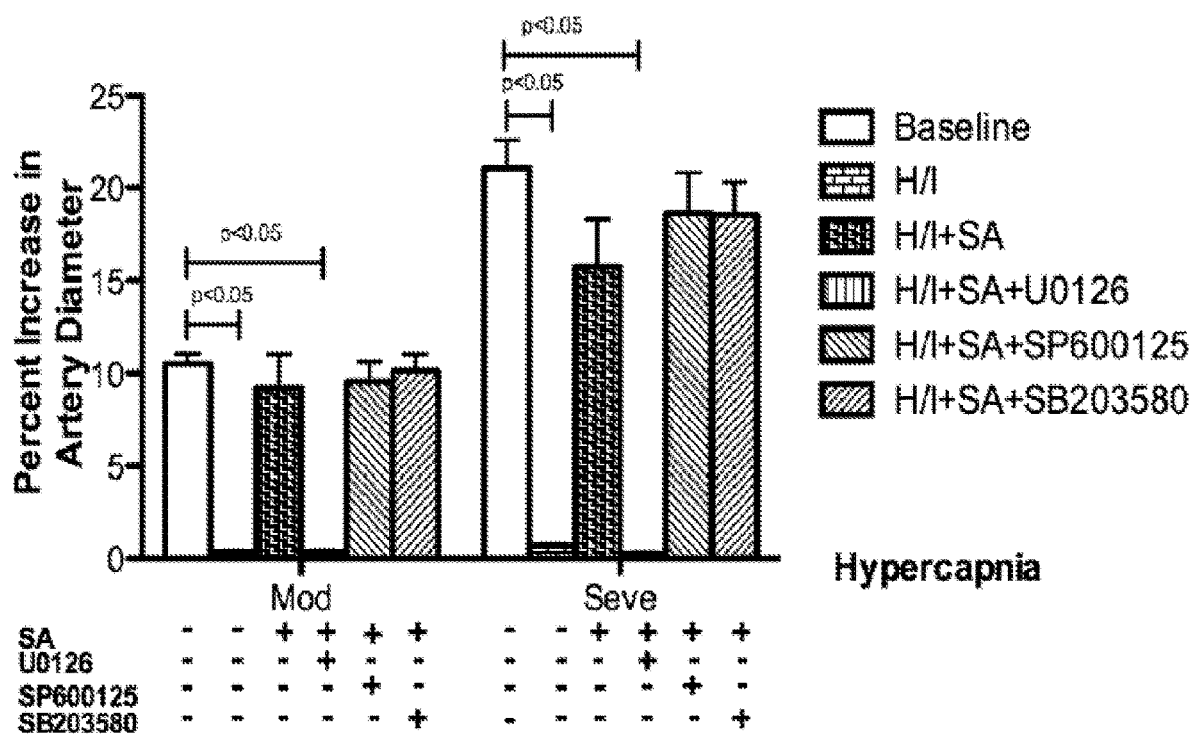

FIG. 15 shows effects of hypercarbia on pial artery diameter before (baseline), after hypoxia/ischemia (H/I; $PO_2$ of 35 mm Hg for 10 minutes followed by global cerebral ischemia for 20 minutes), after H/I pretreated with salvinorin A (10 μg/kg i.v.; H/I+SA) 30 minutes before H/I, and after H/I pretreated with U0126 (1 mg/kg, i.v.; H/I+SA+U0126), the antagonist of ERK, 30 minutes before salvinorin A, SP600125 (1 μM, administrated topically; H/I+SA+SP600125), the antagonist of JNK, 30 minutes before salvinorin A, SB203580 (10 μM, administrated topically; H/I+SA+SB203580), the antagonist of P38, 30 minutes before salvinorin A. Pretreatment with salvinorin A preserved the dilation response of pial artery to hypercarbia, which is abolished by U0126. SA: Salvinorin A; H/I: Hypoxia/ischemia; Moderate: moderate hypercapnia with $PaCO_2$ of 50 to 60 mmHg; Severe: severe hypercapnia with $PaCO_2$ of 70 to 80 mmHg.

Figure 16:
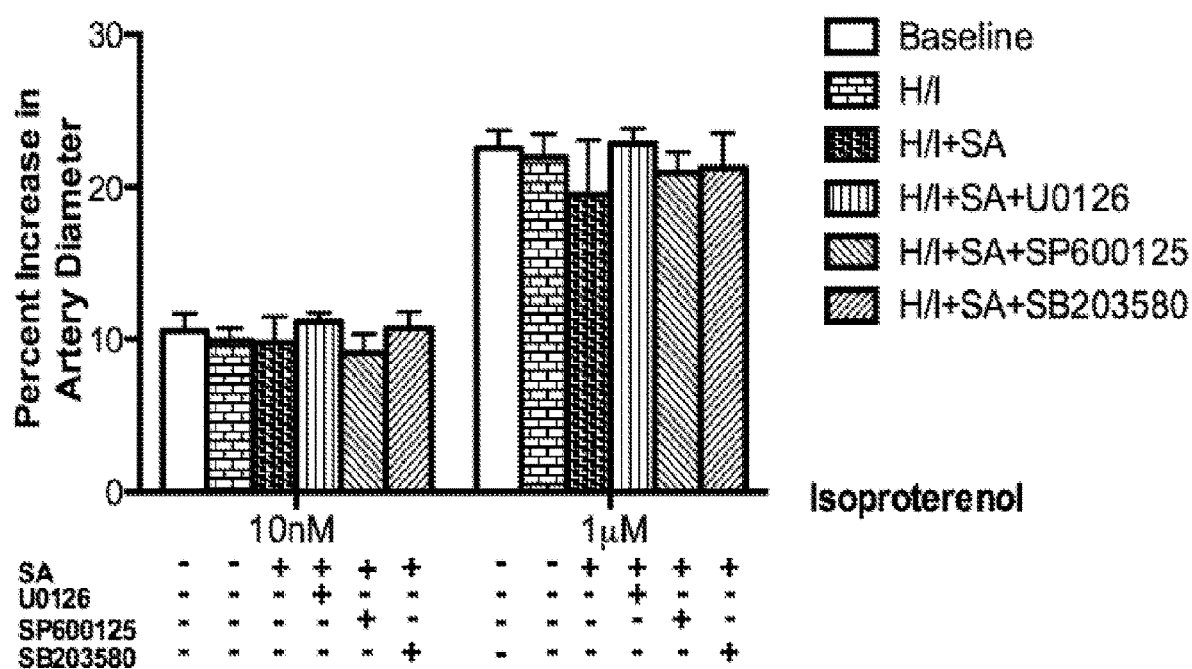

FIG. 16 shows effects of isoproterenol (10 nM, 1 μM) on pial artery diameter before (baseline) and after hypoxia/ischemia did not change significantly in the presence and absence of various interventions. SA: Salvinorin A; H/I: Hypoxia/ischemia.

Figure 17:
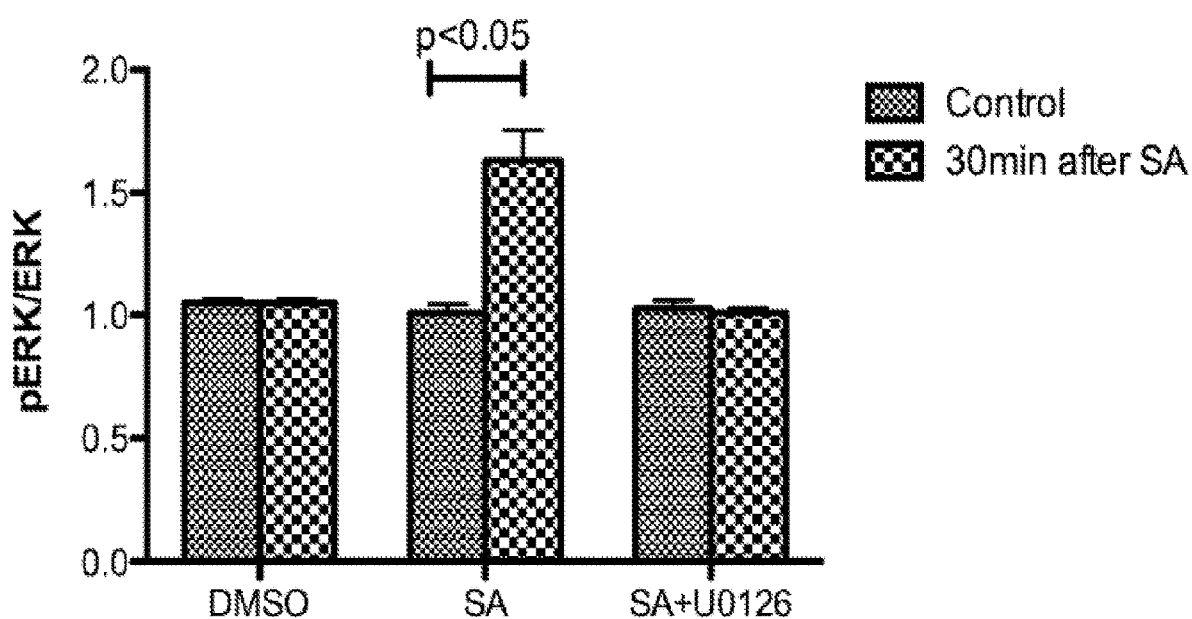

FIG. 17 shows the ratio of pERK/ERK before administration of salvinorin A and 30 minutes after pretreatment of salvinorin A or U0126 plus salvinorin A. The ratio of pERK/ERK in CSF increased significantly 30 minutes in the salvinorin A pretreatment group; and such increase was abolished by the ERK antagonist (U0126) pretreatment SA: Salvinorin A. H/I: Hypoxia/ischemia.

DETAILED DESCRIPTION OF THE INVENTION

The invention relates to salvinorin compositions and uses thereof. Specifically, the invention relates to administering a salvinorin compound to produce vasodilatory effect and sedative effect. The invention further relates to treating various diseases or disorders.

In one embodiment, provided herein is a method for producing a cerebrovasodilation in a subject, the method comprising: administering to said subject a therapeutically effective amount of a salvinorin or a pharmaceutical composition thereof, thereby producing said cerebrovasodilation. In another embodiment, provided herein is a method for treating a disease associated with a cerebrovasospasm in a subject, the method comprising: administering to said subject a therapeutically effective amount of a salvinorin or a pharmaceutical composition thereof, thereby treating said disease.

In another embodiment, provided herein is a method for treating a disease associated with a vascular dilation in a subject, the method comprising: administering to said subject a therapeutically effective amount of a salvinorin or a pharmaceutical composition thereof, thereby treating said disease. In another embodiment, provided herein is a method for producing a sedative or anesthetic effect in a subject, the method comprising: administering to said subject a therapeutically effective amount of a salvinorin or a pharmaceutical composition thereof, thereby producing said sedative or anesthetic effect.

In another embodiment, provided herein is a pharmaceutical composition comprising: a therapeutically effective amount of a salvinorin, wherein said salvinorin is present in an amount effective to produce a cerebrovasodilation in a subject. In another embodiment, provided herein is a pharmaceutical composition comprising: a therapeutically effective amount of a salvinorin, wherein said salvinorin is present in an amount effective to treat a disease associated with a cerebrovasospasm or ischemia in a subject.

In another embodiment, provided herein is a pharmaceutical composition comprising: a therapeutically effective amount of a salvinorin, wherein said salvinorin is present in an amount effective to produce a organ protection from hypoxia/ischemia in a subject. In another embodiment, provided herein is a pharmaceutical composition comprising: a therapeutically effective amount of a salvinorin, wherein said salvinorin is present in an amount effective to treat a disease associated with a vasodilation in a subject.

In another embodiment, provided herein is a pharmaceutical composition comprising: a therapeutically effective amount of a salvinorin, wherein said salvinorin is present in an amount effective to treat a disease associated with a sedative or antinociceptive effect in a subject.

Figure 7:
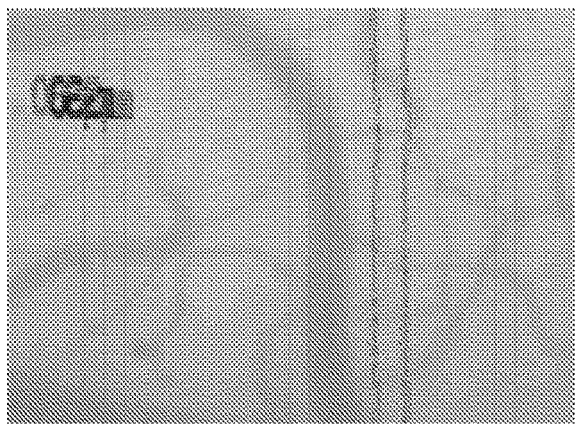
Figure 7:
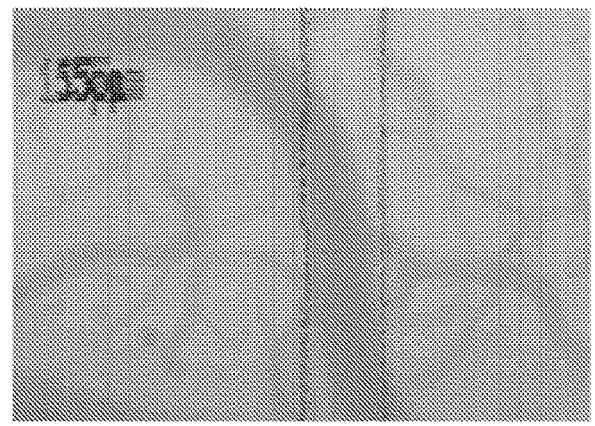
Figure 9:
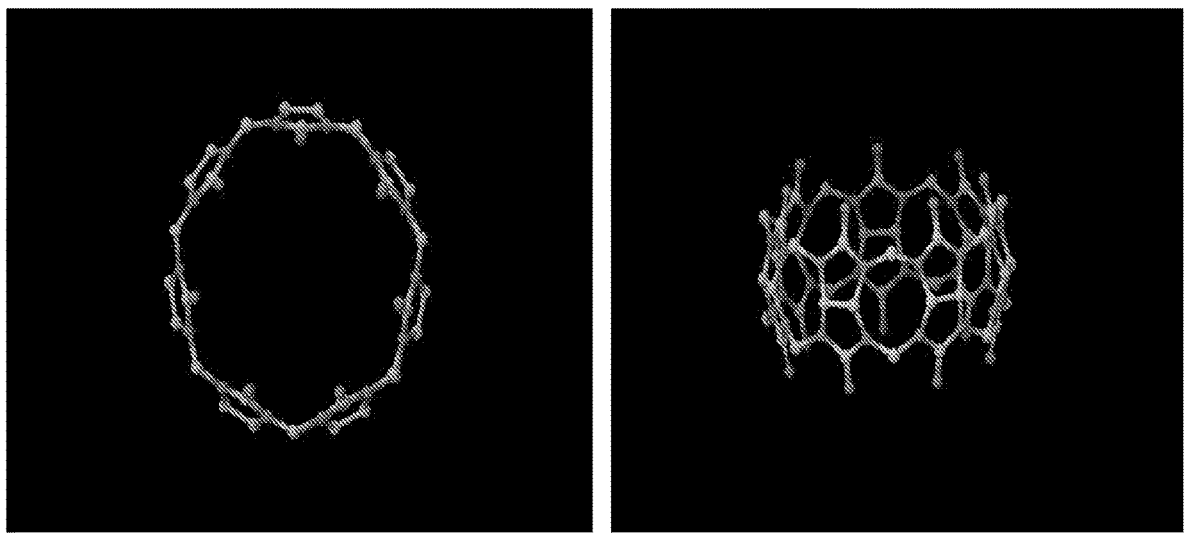

The inventor of the instant application surprisingly and unexpectedly found that salvinorin dilates cerebral vessels dramatically with rapid onset and offset, and without a change in hemodynamics. The diameter of the cerebral artery dilated up to 40% with 1 micro molar salvinorin as shown in FIG. 7. The vessels dilated immediately after application of salvinorin and the dilation effect lasted less than 3 to 5 minutes. This finding demonstrates that a salvinorin compound can be used to treat cerebral vascular spasm in stroke, brain injury, or other related clinical situations associated with cerebral vascular spasm.

Salvinorin A and its analogues are known compounds. Salvinorin A, the active component of *Salvia Divinorum* which is used by nearly million people as recreational purpose annually in United States, is the only known non-nitrogenous selective kappa opioid receptor (KOR) agonist.

A diterpene salvinorin A has recently been shown to be a high affinity and selective kappa opioid receptor agonist. See Roth et al., Proc. Natl. Acad. Sci. USA 99:11934 (2002); and Butelman et al., Psychopharmacology 172:220 (2004).

Salvinorins and their derivatives are well known in the art. For example, salvinorins, their derivatives, and methods for synthesizing them are fully described in U.S. 2006/0052439, U.S. 2007/0213394, WO 2005/089745, and WO2008/119097, all of which are incorporated by reference herein in their entirety.

Any salvinorin or its derivative, known to one of skilled in the art, may be used for producing a vasodilation of the invention as well as for treating a disease associated therewith. Examples of a salvinorin include, but are not limited to, salvinorin A, B, C, D, E, or F. In one embodiment, salvinorin is salvinorin A. In another embodiment, salvinorin is salvinorin B. In another embodiment, salvinorin is salvinorin C. In another embodiment, salvinorin is salvinorin D. In another embodiment, salvinorin is salvinorin E. In another embodiment, salvinorin is salvinorin F. In another embodiment, salvinorin is an ester of a salvinorin. In another embodiment, salvinorin is a salvinorin benzoate. In another embodiment, salvinorin is a metabolite of salvinorin. In another embodiment, salvinorin is a analogue of salvinorin A.

According to one embodiment of the invention, administering a therapeutically effective amount of a salvinorin produces a vasodilation in a subject.

The invention further provides methods of treating a disease or condition, comprising administering to a mammal in need thereof a therapeutically effective amount of a salvinorin.

In one embodiment, the invention provides a method for treating a disease associated with a vasodilation in a subject, the method comprising: administering to said subject a therapeutically effective amount of a salvinorin or a pharmaceutical composition thereof, thereby treating said disease.

The pharmaceutical compositions of the invention may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented.

Examples of disease or disorder caused by or otherwise associated with vasodilation, include, but are not limited to, a cerebral vascular spasm, a stroke, a brain trauma or injury, an ischemia reperfusion injury, low perfusion status, and hypoxia.

The salvinorins of the present invention and pharmaceutical compositions comprising the same can be, in another embodiment, administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally, intrathecally, and inhalationally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound (e.g. the mimetic compound, peptide or nucleotide molecule) and the inert carrier or diluent, a hard gelating capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Topical formulations include, in another embodiment, gels, ointments, creams, lotions, drops and the like.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of active agent over a period of time.

In another embodiment, the active compound is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media.

Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In another embodiment, the composition is an immediate-release composition, i.e. a composition in which of the active compound is released immediately after administration.

In another embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the target cell, thus requiring only a fraction of the systemic dose (see, e.g., Goodson, in Medical Applications of Controlled Release, supra, vol. 2, pp. 115-138 (1984); and Langer R, Science 249: 1527-1533 (1990).

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, cyclodextrin, cucurbituril, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compounds solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Each of the above additives, excipients, formulations and methods of administration represents a separate embodiment of the present invention.

In one embodiment, the methods of the present invention comprise administering an active compound as the sole active ingredient. However, also encompassed within the scope of the present invention are methods for treating diseases and disorders that comprise administering the active compound in combination with one or more therapeutic agents. In another embodiment, these agents are appropriate for the disease or disorder that is being treated, as is well known in the art.

The other therapeutically effective agent may be conjugated to the salvinorin, incorporated into the same composition as the salvinorin, or may be administered as a separate composition. The other therapeutically agent or treatment may be administered prior to, during and/or after the administration of the salvinorin.

The administration of the salvinorin with other agents and/or treatments may occur simultaneously, or separately, via the same or different route, at the same or different times. Dosage regimens may be adjusted to provide the optimum desired response (e.g., a therapeutic or prophylactic response).

Effective doses of the compositions of the present invention, for treatment of conditions or diseases as described herein vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

In one example, a single bolus may be administered. In another example, several divided doses may be administered over time. In yet another example, a dose may be proportionally reduced or increased as indicated by the exigencies of the therapeutic situation. Dosage unit form, as used herein, refers to physically discrete units suited as unitary dosages for treating mammalian subjects. Each unit may contain a predetermined quantity of active compound calculated to produce a desired therapeutic effect. In some embodiments, the dosage unit forms of the invention are dictated by and directly dependent on the unique characteristics of the active compound and the particular therapeutic or prophylactic effect to be achieved.

The composition of the invention may be administered only once, or it may be administered multiple times or continues infusion. For multiple dosages, the composition may be, for example, administered three times a day, twice a day, once a day, once every two days, twice a week, weekly, once every two weeks, or monthly.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

"Administration" to a subject is not limited to any particular delivery system and may include, without limitation, parenteral (including subcutaneous, intravenous, intramedullary, intraarticular, intramuscular, or intraperitoneal injection) rectal, topical, transdermal or oral (for example, in capsules, suspensions or tablets), intrathecal, and inhaltional. Administration to a host may occur in a single dose or in repeat administrations or continuous infusion, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, for example, Remington's Pharmaceutical Sciences, Mack Publishing Co.).

As used herein, a "composition" refers to any composition that contains a pharmaceutically effective amount of a salvinorin compound.

The methods of treatment described herein can be used to treat any suitable mammal, including primates, such as monkeys and humans, horses, cows, cats, dogs, rabbits, and rodents such as rats and mice. In one embodiment, the mammal to be treated is human.

Any reference including patents, patent applications, or scientific publications, cited herein, are incorporated by reference in their entirety.

The following examples are presented in order to more fully illustrate the preferred embodiments of the invention. They should in no way be construed, however, as limiting the broad scope of the invention.

EXAMPLES

Example 1

Salvinorin A Produces Cerebrovasodilation through Release of Nitric Oxide and Activation of Kappa Receptor and ATP Sensitive Potassium Channel In the present study, the inventors have shown that salvinorin A dilates pial arteries under resting tone conditions as well as during elevated tone conditions such as during hypocapnia induced by hyperventilation via release of nitric oxide and activation of KATP channels. Salvinorin A produces vasodilatation in normal and constricted cerebral arteries induced by hypocapnia. The mechanisms of the dilation involve activation of nitric oxide synthase, Katp channel and the opioid receptor.

Materials and Methods

Salvinorin A, sodium nitroprusside (SNP), N(G)-nitro-L-arginine (L-NNA), glibenclamide, iberiotoxin, cromakalim, calcitonin-gene related polypeptide (CGRP), NS1619, naloxone, methionine enkephalin and isoproterenol are all obtained from Sigma-Aldrich (MO, St. Louis, Mo., USA). All other chemicals were also obtained from Sigma and were of reagent grade.

Animals and Surgery

Newborn pigs (1-6 days old, weighing 1.3-1.8 kg) of both genders were used for this study. Protocols were approved by the Institutional Animal Care and Use Committee of the University of Pennsylvania. The animals were induced with isoflurane (1-2 MAC) and then maintained with alpha-chloralose (80-100 mg/kg supplemented with 5 mg/kg/h IV). Both femoral arteries were catheterized to monitor blood pressure and blood gas. A catheter was inserted into right femoral vein for medication administration. The animals were ventilated with room air after trachea cannulation. Rectal temperature was maintained at 37-39° C. by a heating pad. A closed cranial window was placed as described previously for direct pial artery visualization and diameter measurement. The closed cranial window consisted of three parts: a stainless steel ring, a circular glass cover-slip, and three ports consisting of 17-gauge hypodermic needles attached to three precut holes in the stainless steel ring. Cortical periarachnoid cerebrospinal fluid (CSF) was collected through the cranial window port for cGMP determination. Before placing the window, the scalp was reflected and an opening was made in the skull over the parietal cortex. Then the dura mater was cut and retracted over the bone edge. The cranial window was placed on the cranial opening and cemented in place with dental acrylic. The space under the window was filled with artificial CSF with the following composition (in mM): 3.0 KCl, 1.5 MgCl2, 1.5 CaCl2, 132 NaCl, 6.6 Urea, 3.7 Dextrose, and 24.6 NaHCO3 per liter, pH 7.33, PCO2 46 mmHg and PO2 43 mmHg. The artificial CSF was warmed to 37-38° C. before application to the cerebral cortical surface. Pial arteries were observed with a television camera mounted on a dissecting microscope. Vascular diameter was measured from a video monitor connected the camera with a video microscaler (model VPA 550, For-A-Corp., Los Angeles, Calif.).

Experimental Protocols

Pial artery diameter (small artery diameter 120-160 micro meter; arteriole diameter 50-70 micro meter) was monitored and recorded every half minute for 10-min after injection of artificial CSF in the presence or absence of the investigated drug. In general, the window was flushed over 30 s with 1-2 ml CSF through the port connected into the side of the window. CSF samples were collected for cGMP analysis before and at 10 min after medication administration. We collected the cerebral cortical periarachnoid CSF by slowly infusing CSF into one port of the window and allowing the CSF to drip freely into a collection tube on the opposite port. Responses to salvinorin A (10 nM, 1 μM, dissolved with alcohol) and sodium nitroprusside (SNP) (10 nM, 1 μM), were obtained in the absence and presence of N(G)-nitro-L-arginine (L-NNA, 1 μM), a nitric oxide synthase (NOS) inhibitor. Additionally, the influences of glibenclamide (100 nM), a KATP channel antagonist, iberiotoxin (100 nM, Sigma-Aldrich), a KCa channel antagonist on pial artery response to salvinorin A, cromakalim (1 μM) and CRRP (10 nM, 1 μM), a KATP agonist, and NS1619 (10 nM, 1 μM), a KCa channel agonist, were also determined. Finally, the effect of naloxone (1 mg/kg IV) on the response to the salvinorin A, methionine enkephalin (10 nM, 1 μM) and isoproterenol (10 nM, 1 μM), a beta adrenergic receptor agonist, were also investigated. All tested drug solutions were made fresh on the day of use.

cGMP Determination

To determine the role of nitric oxide pathway on the effect of salvinorin on cerebral vasculature, CSF samples were collected for cGMP determination before and after salvinorin A administration with or without L-NNA pretreatment. Commercially available ELISA kits (Assay Designs, Michigan, US) were used to quantify cGMP concentration.

Salvinorin A on Constricted Vessels

To test the cerebrovascular effect of salvinorin during elevated cerebrovascular tone, we induced vasoconstriction via hyperventilation to reduce carbon dioxide (PaCO2) in blood by 20-30% for 10 min. The pial artery diameter changes were monitored at baseline, after CO2 reduction, and after salvinorin A (10 nM, 1 μM) administration (n=4).

Statistical Analysis

All data (diameters and cGMP) were analyzed using ANOVA with repeated measures. If statistical significance is observed, the data were then analyzed using Fisher's test. A level of $p<0.05$ was considered statistically significant. Values are represented as mean±SEM of the absolute value; or as percentage changes from the baseline values.

Results

Dilation Effect and the Role of Nitric Oxide Pathway

Figure 2:
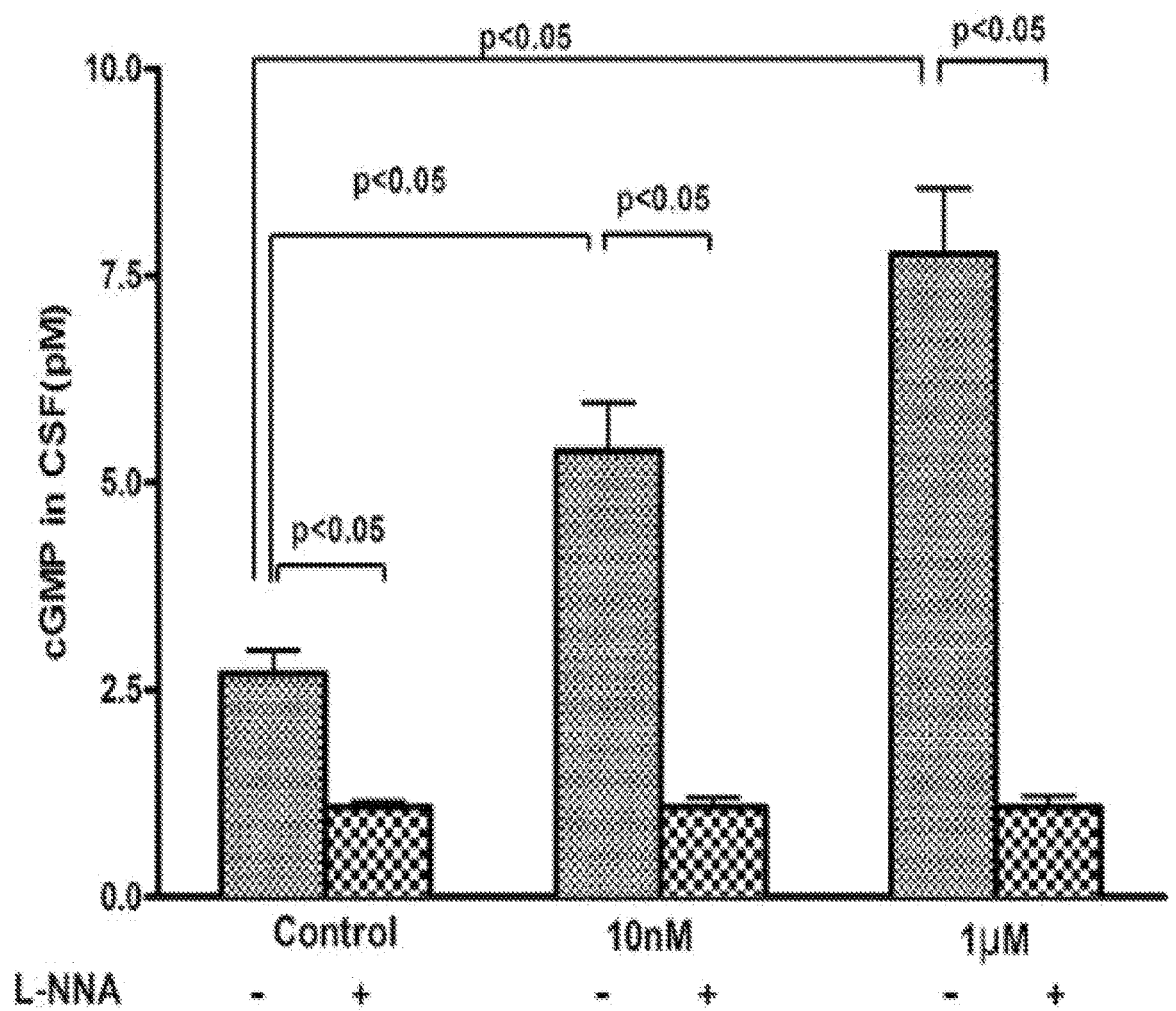

Salvinorin A dose dependently (10 nM, 1 μM) dilated the pial artery of piglet as shown in FIG. 1. The dilation effect is observed immediately after salvinorin administration and the duration of dilation lasted less than 5 minutes for both doses. The dilation response was abolished by L-NNA, the NOS inhibitor. In contrast, dilation in response to sodium nitroprusside (SNP) was not affected by L-NNA (FIG. 1). Dilation in response to salvinorin A was associated with elevated cGMP in CSF, and L-NNA blocked the elevation of the cGMP (FIG. 2). No significant blood pressure changes during salvinorin administration.

KATP Channel, not KCa Channel, Involves in the Dilatation Effect

Figure 3:
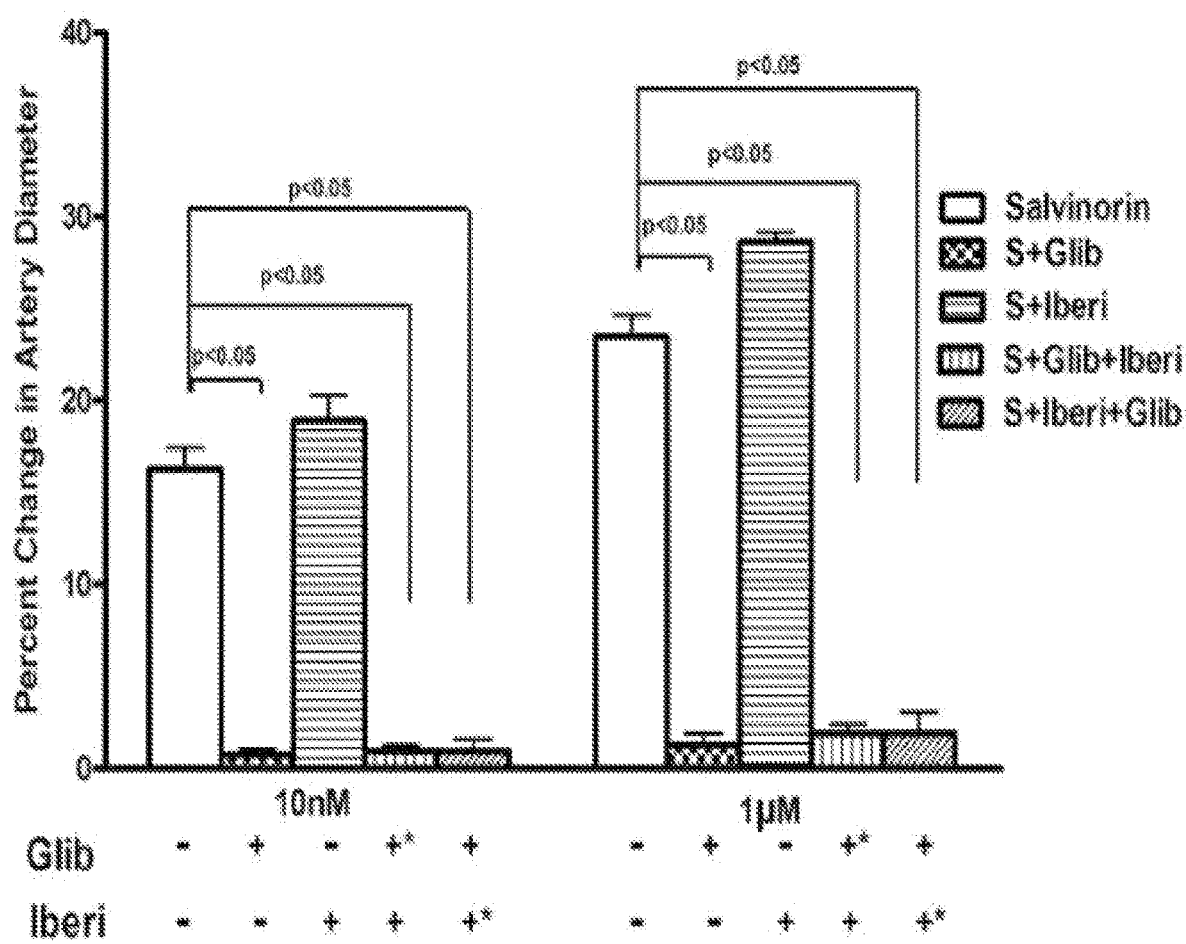
Figure 4:
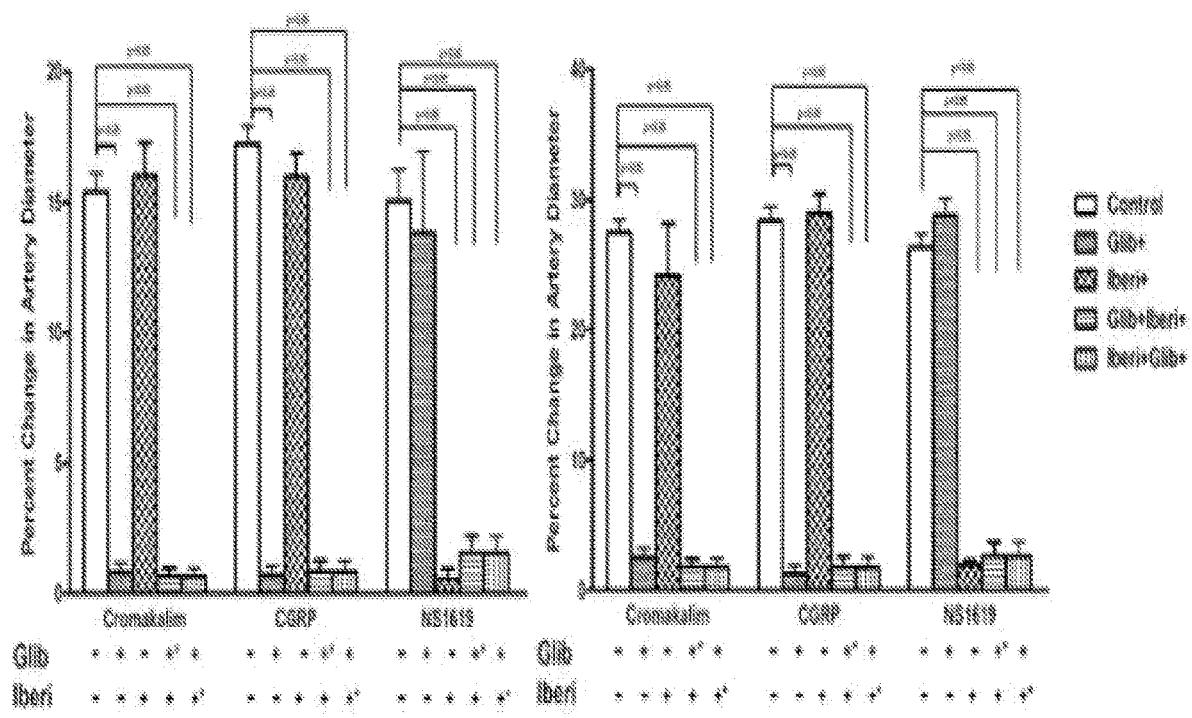

Glibenclamide (100 nM), the ATP sensitive potassium (KATP) channel inhibitor but not iberiotoxin (100 nM), the Ca2+-activated K+ (KCa) channel inhibitor, blocked the dilation effects of salvinorin A. Glibenclamide with iberiotoxin in any sequence also blocked the dilation induced by salvinorin A (FIG. 3). Glibenclamide (100 nM) but not iberiotoxin (100 nM) blocked the dilation in response to cromakalim (an agonist of KATP channel, 10 nM and 1 μM) and CGRP (another KATP channel agonist, 10 nM and 1 μM); iberiotoxin (100 nM) but not glibenclamide (100 nM) blocked the dilation effects of NS1619 (agonist of KCa channel, 10 nM and 1 μM. FIG. 4).

Opioid Receptor Antagonist Blocked Dilation Effect of Salvinorin

Figure 5:
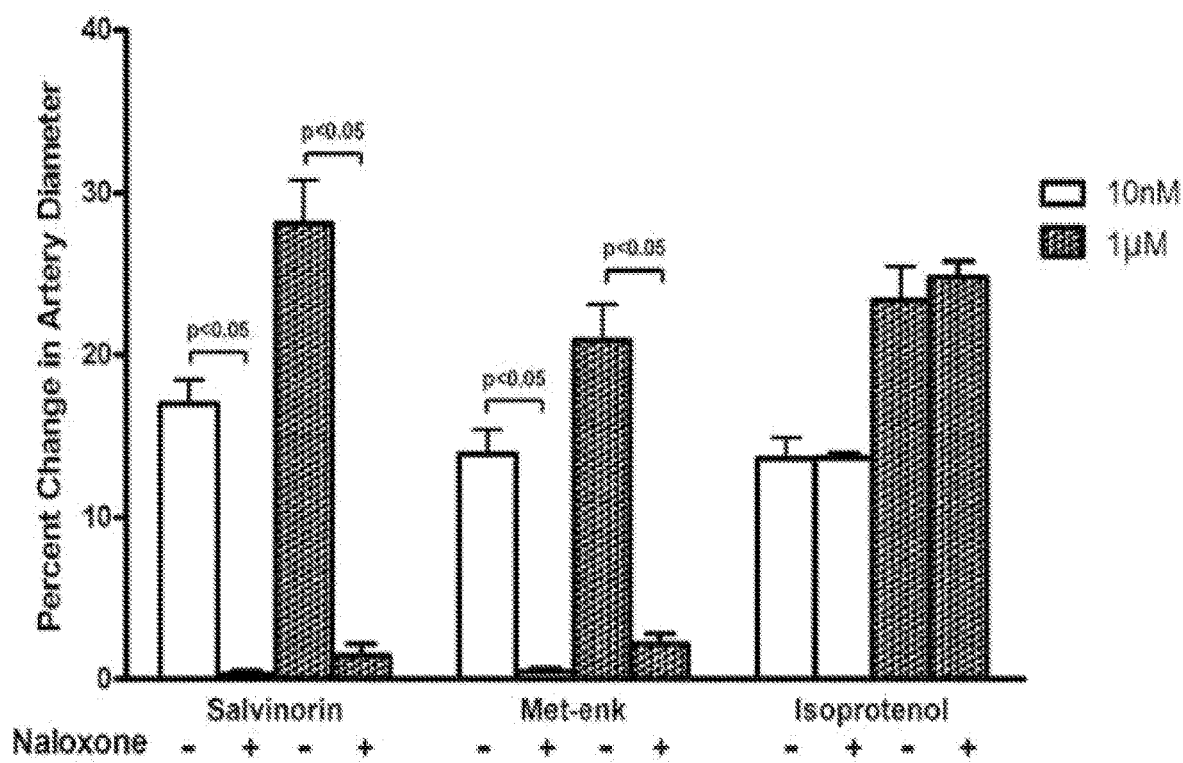

Naloxone (1 mg/kg IV) blocked the dilatation effects to salvinorin A and methionine enkephalin while responses to isoproterenol were unchanged (FIG. 5).

Salvinorin Dilates Pial Arteries in Elevated Cerebrovascular Tone Conditions

Figure 6:
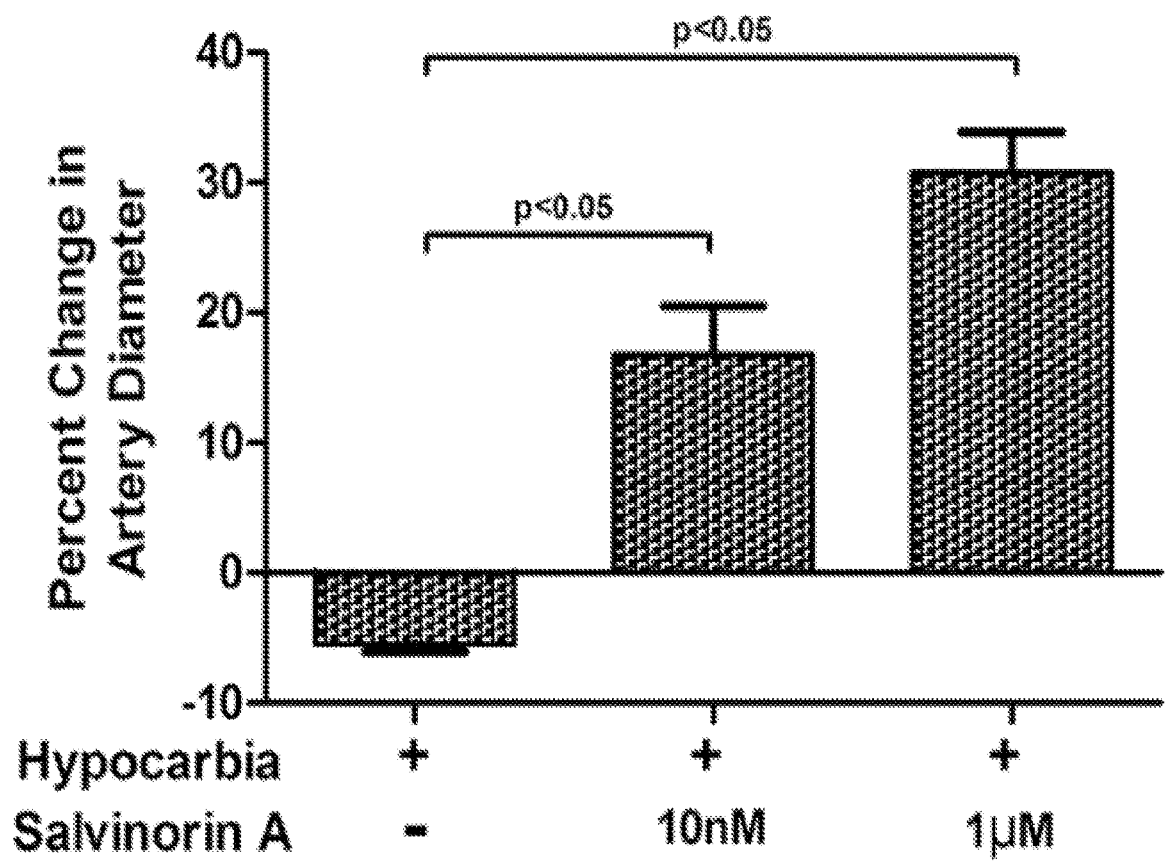

Hypocapnia significantly decreased the diameter of pial arteries (FIG. 6). Salvinorin dilated pial arteries under elevated tone conditions similar to that observed under normocapnic (resting tone) conditions (FIG. 6).

In the present study, we demonstrated that salvinorin A is a potent pial artery dilator in piglet in normal and vessel constricted condition induced by changing CO2 level. The dilatation effect was observed immediately after salvinorin administration, lasted less than 5 min for both tested doses, and dose-dependent. The activation of the opioid receptor, NOS and KATP channel were involved in the signal pathway of such dilation effects.

The unique structure of salvinorin A contributes to its short acting character. Ester linkage in its structure can be easily metabolized by esterase in the blood and tissues.

KATP channels activation may result in hyperpolarization of the membrane of vascular smooth muscle cell. Membrane potential changes would then regulate muscle relaxation through alterations in Ca2+ influx through voltage-dependent Ca2+ channels.

We have shown that salvinorin A is an agonist of KATP channel. Different from other KATP channel agonists, salvinorin A can easily penetrate the blood-brain barrier. Since KATP channel play a crucial protective role against brain injury from hypoxia, ischemia or metabolic inhibition, salvinorin A might be a potential neuro-protective agent for possible clinical usage in the future. The vascular dilative effective observed in normal and constricted cerebral vessels shows salvinorin's clinical application to treat the cerebral vessel spasm in many clinical situations including migraine and cerebral vascular spasm after subarachnoid hemorrhage.

In the present study, newborn piglets were used as the study subject. The gyrencephalic brain of pig has more white than gray matter which is selectively vulnerable to injury similar to the human, and also similar in maturity. The new born piglet is also used because it is large enough for easy cranial window placement and vascular visualization. The newborn's cerebral vascular responses are similar to that in human subjects in many clinical situations and there is no report so far indicating that their responses are different.

In conclusion, salvinorin A is a fast and short acting potent pial artery dilator in piglet in normal and vessel constricted condition induced by changing CO2 level. The mechanism involves the activation of NOS, KATP channel and opioid receptor. These findings demonstrate that salvinorin A has clinical values in the setting of demanding cerebral vascular dilation.

Example 2

Cerebral Vascular Autoregulation to Hypercarbia and Hypertension is Preserved After Hypoxia/Ischemia with Salvinorin Administration Cerebral vascular autoregulation to both hypercarbia and hypertension preserved very well with salvinorin administration immediately after global brain hypoxia and ischemia (n=3)

As shown in FIG. 13, upper panel, cerebral vascular autoregulation to hypercabia was preserved very well with salvinorin administration immediately after global brain hypoxia and ischemia (n=3). As shown in FIG. 13, lower panel, cerebral vascular autoregulation was disrupted after hypoxia/ischemia (HI). Similar results were observed for hypertension.

Example 3

Salvinorin A Pretreatment Preserves Cerebrovascular Autoregulation After Brain Hypoxic/Ischemic Injury Via ERK/MAPK in Piglets Cerebral hypoxia/ischemia during infant congenital heart surgery is not uncommon, and may induce devastating neurologic disabilities persistent over the life span. Hypoxia/ischemia induced cerebrovascular dysfunction is thought to be an important contributor to neurological damage. No pharmacological agents have been found to prevent this. Mitogen activated protein kinase (MAPK) including extracellular signal regulated kinase (ERK), c-Jun-N-terminal kinase (JNK) and p38, is thought to contribute to ischemic pre-conditioning. We investigated whether pretreatment with salvinorin A, the only natural non-opioid kappa receptor agonist, could preserve autoregulation of pial artery via MAPK.

We have found that Salvinorin A pretreatment preserves the autoregulation of pial artery to hypotension and hypercapnia after hypoxia/ischemia via ERK in a piglet model.

Methods

Salvinorin A (purity ≥98%) is from ChromaDex, Inc. (Irvine, Calif., USA). Isoproterenol, U0126, sp600125 and sb203580 are obtained from Sigma-Aldrich (MO, St. Louis, Mo., USA). All other chemicals were also obtained from Sigma and were of reagent grade.

Animals and Surgery

One to five days old piglets were used. Protocols were approved by the Institutional Animal Care and Use Committee of the University of Pennsylvania (Philadelphia). Isoflurane (1-2 minimum alveolar concentration) was initially used for induction, followed by alpha-chloralose for maintenance of anesthesia (30-100 mg/kg, supplemented with 5-30 mg/kg every 20-30 min IV). After tracheotomy, piglets were mechanically ventilated with room air and kept warm with a heating pad, maintaining rectal temperature at 37 to 39° C. Femoral arteries were cannulated for continuous blood pressure monitoring or intermittent blood gas monitoring, and the femoral vein was catheterized for medication administration. As described previously, a closed cranial window was placed for direct pial artery visualization and diameter measurement. Small pial artery (120 to 160 µm) and arteriole (50 to 70 µm) are identified under microscope, visualized on a monitor connected to the microscope, and measured via a video microscaler (model VPA 550, For-A-Corp., Los Angeles, Calif.). The cranial window is a steel ring with a glass cover slip, connecting to three ports for cerebrospinal fluid (CSF) sampling, washout and medicine administration. Cortical periarachnoid CSF was collected through one of the above ports at baseline and 30 minutes after administration of salvinorin A or U0126 plus salvinorin A for ERK/MAPK analysis.

Protocol

Hypoxia was induced for 10 minutes by switching room air to $N_2$ for ventilation, followed by restoring ventilation to room air; and then global cerebral ischemia was induced by infusing saline through a hollow bolt in the cranium to maintain intracranial pressure higher than the mean blood pressure for 20 min. Global ischemia is confirmed when the blood flow in pial artery stopped, visualized on the monitor connected to the microscope over the cranial window. In order to avoid Cushing response (arterial pressure rising dramatically because of high intracranial pressure), blood was withdrawn when necessary to maintain mean arterial blood pressure no higher than 100 mmHg The blood was returned via femoral vein at the end of ischemia.

Five sets of experiments were performed (n=5 in each set of experiment): (1) hypoxia/ischemia with vehicle of salvinorin A, DMSO, 1 µl/kg administrated 30 minutes before hypoxia/ischemia; (2) hypoxia/ischemia with salvinorin A, 1 µg/µl in DMSO, 10 µg/kg i.v.; (3) hypoxia/ischemia with salvinorin A (10 µg/kg i.v.) and U0126 (1 mg/kg, i.v.), an inhibitor for the protein kinases upstream of ERK, (4) hypoxia/ischemia with salvinorin A and sp600125 (1 µM, topically injected through one port of cranial windows), an inhibitor of JNK, (5) hypoxia/ischemia with salvinorin A and sb203580 (10 µM, topically injected through one port of cranial windows), an inhibitor of $P_{38}$. U0126, sp600125 and sb203580 are administrated 30 minutes before salvinorin A. Sp600125 and sb203580 were co-administered with the vasoactive stimulus so as to have continued exposure of the cerebral cortical surface after injury.

Hypercapnia ($PaCO_2$ of 50 to 60 mmHg for low level, 70 to 80 mmHg for high level) was produced by inhalation of high concentration $CO_2$ mixture gas (10% $CO_2$; 21% $O_2$; 69% $N_2$). Hypotension was produced by withdrawing blood from the femoral artery (25% decrease in mean blood pressure as moderate and 45% as severe). Pial artery responses to hypotension, hypercapnia, and isoproterenol (10 nM, 1 µM) were obtained before hypoxia/ischemia and 60 minutes after injury as described previously (22).

ERK and pERK Measurement

To test the role of ERK on the observed effects of salvinorin A on brain hypoxia/ischemia, CSF samples were collected for MAPK. MAPK isoforms were measured by commercially available ELISA kits (Enzo Life Sciences International, Inc., Plymouth Meeting, Pa.).

Statistical Analysis

The percentages changes of pial artery diameter to every stimulation (hypotension, hypercapnia and isoproterenol,) from the baseline before and after hypoxia/ischemia were analyzed by repeated-measures ANOVA with a Greenhouse-Geisser correction if Sphericity assumption was not satisfied and followed by post hoc of Bonferroni correction. The same statistical methods were used for the pERK/ERK data to compare the ratio changes before and after administration of salvinorin A. An alpha level of $P<0.05$ was considered significant in all statistical tests. All values are represented as means±standard error.

Results

Salvinorin A Preserved Pial Artery Autoregulation to Hypotension After Hypoxia/Ischemia.

As indicated in FIG. 14, small pial artery dilated to two levels of hypotension at baseline before hypoxia/ischemia. The dilatation response was blunted after hypoxia/ischemia. Pretreatment with salvinorin A (10 µg/kg, iv.) preserved the dilation response of pial artery to hypotension. This is abolished by U0126, the antagonist of ERK. No changes in the preservative effects were observed from SP600125 (antagonist of JNK) and SB203580 (antagonist of $P_{38}$) administered 30 minutes before administration of salvinorin A. Similar observations were obtained in pial arterioles.

Salvinorin A Preserved Pial Artery Autoregulation to Hypercapnia After Hypoxia/Ischemia.

Similar to the response to hypotension, small pial artery dilated to two levels of hypercapnia at baseline before hypoxia/ischemia (FIG. 15). The dilatation response was blunted after hypoxia/ischemia. Pretreatment with salvinorin A (10 μg/kg, iv.) preserved the dilation response of pial artery to hypercapnia. This is abolished by U0126, the antagonist of ERK. No change in the preservative effects was observed from SP600125 and SB203580 administered 30 minutes before administration of salvinorin A. Similar observations were obtained in pial arterioles.

Pial Artery Response to Isoproterenol Unchanged in All Sets of Experiments

As a positive control and indicated in FIG. 16, pial artery response to isoproterenol was unchanged in all groups before and after hypoxia/ischemia in the presence or absence of the above interventions.

ERK Involved in the Preservation Effects of Salvinorin A

The ratio of pERK/ERK in CSF increased significantly 30 minutes after salvinorin A pretreatment (FIG. 17). However, if U0126, the antagonist of ERK, was administrated 30 minutes before salvinorin administration, the ratio of pERK/ERK was unchanged 30 minutes after salvinorin A pretreatment (FIG. 17).

There are two principal new findings in this study. Firstly, pretreatment of salvinorin A preserved cerebrovascular autoregulatory ability after hypoxia/ischemia. Secondly, ERK/MAPK is involved in the ability of salvinorin A to preserve autoregulation.

In this study we demonstrated that salvinorin A pretreatment preserved the autoregulatory responses to hypotension and hypercapnia after hypoxia/ischemia in a piglet model, which may lead to its clinical application to attenuate cerebral hypoxia/ischemia, especially for brain ischemia during DHCA in infant.

In conclusion, salvinorin A pretreatment preserved cerebrovascular autoregulation to hypotension and hypercapnia after brain hypoxia/ischemia via ERK/MAPK in a piglet model.

Example 4

Salvinorin as an Adjunctive Medication for Difficult Airway Management

We often have to manage a patient's airway in the awake (unanesthetized) state when difficult airway is an issue, but partial sedation facilitates patient comfort and conduct of the procedure. An ideal sedative should meet the following criteria: (1) be sedative; (2) have a rapid onset; (3) be short acting; (4) inhibit coughing; (5) have minimal respiratory inhibition; (6) have minimal hemodynamic effects, and (7) be easy to be deliver intravenously. Salvinorin A, however, can meet these criteria, at least based on data available in the literature. It is a kappa opioid receptor agonist which has sedative and dissociative effects, inhibits cough and has minimal respiratory depressive effects, at least as compared to conventional mu receptor agonists (morphine). It has fast onset and offset with minimal hemodynamic changes. Thus, salvinorin can be useful during awake intubation. However, salvinorin is poorly soluble in water. One option is to use its salt form to increase water solubility, and the other is to use lipid emulsion. Both techniques are readily available and have been successfully used for other anesthetic drugs in the perioperative settings. Cucurbituril (FIG. 11) could be used as a carrier. As shown in FIGS. 12-13, salvinorin and cucurbituril complex can be used.

Another concern related to this medication is its dysphoric effects, which can be addressed with short-acting benzodiazepines like midazolam.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for treating cerebral vascular spasm after a subarachnoid hemorrhage, in a subject having a cerebral vascular spasm, the method comprising:

administering to said subject a therapeutically effective amount to induce cerebrovasodilation of a salvinorin A or a pharmaceutical composition thereof, thereby treating said cerebral vascular spasm.

2. The method of claim 1, wherein said subject is a mammal.

3. A method for preventing and treating cerebral hypoxia/ischemia comprising administering to a subject in need thereof an effective amount of salvinorin A to induce cerebrovasodilation in the subject.

4. The method of claim 3, wherein at least 10 μg/kg of salvinorin A is administered to the subject.

5. The method of claim 3, wherein the salvinorin A is administered during the hypoxia/ischemia.

6. The method of claim 3, wherein the salvinorin A is administered within 30 minutes of the hypoxia/ischemia.

7. The method of claim 3, wherein the salvinorin A is administered within 30 minutes of reperfusion.

8. A method for preventing or treating cerebral vascular spasm after a subarachnoid hemorrhage (SAH) comprising administering to a subject in need thereof an effective amount of salvinorin A to induce cerebrovasodilation in the subject.

9. The method of claim 8, wherein at least 10 μg/kg of salvinorin A is administered to the subject.

10. A method for treating cerebral hypoxia/ishemia associated with a cerebrovasospasm in a subject, the method comprising: administering to said subject a therapeutically effective amount to induce cerebrovasodilation of a salvinorin A or a pharmaceutical composition thereof, thereby treating said disease.

11. A method of producing a cerebrovasodilation in a subject, the method comprising:

administering to said subject a therapeutically effective amount to induce cerebrovasodilation of a salvinorin A or a pharmaceutical composition thereof, thereby producing said cerebrovasodilation.

12. The method of claim 11, wherein the subject is suffering from cerebral hypoxia/ischemia.

* * * * *